United States Patent
Walke et al.

(10) Patent No.: US 8,399,521 B2
(45) Date of Patent: Mar. 19, 2013

(54) METHODS OF TREATING SKIN WITH AROMATIC SKIN-ACTIVE INGREDIENTS

(75) Inventors: Bob Walke, Flower Mound, TX (US); Cristie Gomez, Rowlett, TX (US); Tiffany C. Florence, Dallas, TX (US); Michelle D. Hines, Hickory Creek, TX (US)

(73) Assignee: Mary Kay Inc., Dallas, TX (US)

( * ) Notice: Subject to any disclaimer, the term of this patent is extended or adjusted under 35 U.S.C. 154(b) by 196 days.

(21) Appl. No.: 12/796,820

(22) Filed: Jun. 9, 2010

(65) Prior Publication Data
US 2010/0249222 A1 Sep. 30, 2010

Related U.S. Application Data

(63) Continuation of application No. 12/105,957, filed on Apr. 18, 2008.

(60) Provisional application No. 61/025,631, filed on Feb. 1, 2008.

(51) Int. Cl.
*A61K 31/12* (2006.01)
*A61K 8/35* (2006.01)
*A61K 8/34* (2006.01)

(52) U.S. Cl. ........................... 514/690; 424/401

(58) Field of Classification Search ........................... None
See application file for complete search history.

(56) References Cited

U.S. PATENT DOCUMENTS

| 6,126,930 | A * | 10/2000 | Dubois et al. | 424/73 |
|---|---|---|---|---|
| 6,147,037 | A * | 11/2000 | Gardlik et al. | 510/107 |
| 6,495,497 | B1 | 12/2002 | Sprecker et al. | 510/101 |
| 2003/0206932 | A1 | 11/2003 | Liu et al. | 424/401 |
| 2006/0084589 | A1 | 4/2006 | Vlad et al. | 510/417 |
| 2006/0263308 | A1 | 11/2006 | Brown et al. | 424/59 |
| 2007/0042061 | A1 | 2/2007 | Ribnicky et al. | 424/755 |

FOREIGN PATENT DOCUMENTS

| EP | 1 882 471 | | 1/2008 |
|---|---|---|---|
| EP | 1 997 378 | | 12/2008 |
| EP | 2 014 273 | | 1/2009 |
| FR | 2856295 | A1 * | 12/2004 |
| WO | WO 2006/053458 | | 5/2006 |
| WO | WO 2008/054067 | | 5/2008 |

OTHER PUBLICATIONS

Thorel et al.; FR 2 856 295 A1; 2004; SciFinder abstract; CAPLUS Accession No. 2004:1128505.*
FR 2 856 295 A1; 2004; English Machine translation.*
Office Communication issued in U.S. Appl. No. 12/105,957, dated Jun. 28, 2011.
Office Communication issued in U.S. Appl. No. 12/105,957, dated Nov. 2, 2010.
Office Communication issued in U.S. Appl. No. 12/105,957, dated Aug. 9, 2010.
PCT International Preliminary Report on Patentability issued in International Application No. PCT/US09/32430, dated Aug. 16, 2011.
Zoublis et al., "Clinical aspects and molecular diagnostics of skin aging," *Clinics in Dermatology*, 29:3-14, 2011.
Office Communication issued in Chinese Patent Application No. 200810100531.2, dated Sep. 5, 2011. (English translation).
International Cosmetic Ingredient Dictionary, 10th edition, Gottschalck and McEwen Jr. (eds.), The Cosmetic, Toiletry, and Fragrance Association, Washington, D.C., 2004.
International Search Report and Written Opinion, issued in Application No. PCT/US2009/032430, date of mailing Sep. 16, 2009.
Invitation to Pay Additional Fees issued in Application No. PCT/US2009/032430, dated Jun. 19, 2009.
Jun at al., "Composition for external use for improving drying of skin, containing musk," Database WPI Week, 2005-008683, Aug. 16, 2004.
Kim et al., "The effects of musk T on peroxisome proliferator-activated receptor [PPAR]—α activation, epidermal skin homeostasis and dermal hyaluronic acid synthesis," *Arch. Dermatol. Res.*, 298:273-282, 2006.
Office Action, issued in U.S. Appl. No. 12/105,957, mailed Feb. 4, 2010.
Remington's Pharmaceutical Sciences, 18th Ed. Mack Publishing Company, Easton, PA, pp. 1289-1329, 1990.
Wade, Organic Chemistry, Fifth Edition, Prentice Hall, Upper Saddle River, NJ, 2003.
Office Communication, issued in Korean Patent Application No. 10-2008-0036286, dated Mar. 4, 2011.

* cited by examiner

*Primary Examiner* — Timothy Thomas
(74) *Attorney, Agent, or Firm* — Fulbright & Jaworski L.L.P.

(57) ABSTRACT

A method for treating skin, reducing oxidative damage to a skin cell, reducing lipoxygenase (LO) activity in a skin cell, reducing cyclooxygenase (COX) activity in a skin cell, reducing tumor necrosis factor alpha (TNF-α) in a skin cell, or reduction matrix metalloproteinase enzyme activity in a skin cell comprising contacting skin or a skin cell with an aromatic skin-active ingredient.

2 Claims, No Drawings

METHODS OF TREATING SKIN WITH AROMATIC SKIN-ACTIVE INGREDIENTS

CROSS REFERENCE TO RELATED APPLICATIONS

This application is a continuation of U.S. application Ser. No. 12/105,957, filed Apr. 18, 2008, which claims the benefit of U.S. Provisional Application No. 61/025,631, filed Feb. 1, 2008. The contents of both referenced applications are incorporated by reference.

BACKGROUND OF THE INVENTION

A. Field of the Invention

The present invention relates generally to methods of treating skin. In particular, the present invention concerns topical skin care compositions that include ingredients found to have beneficial effect on skin.

B. Description of Related Art

In the cosmetic industry, certain ingredients (both skin-active and non active ingredients) can have rather unpleasant odors. Such ingredients include nitrogen-containing compounds, heterocyclic compounds, and sulfur-containing compounds. The end result is the production of cosmetic compositions that have foul odors.

Odor neutralizing ingredients have been used to reduce or mask malodorous cosmetic compositions. The use of aromatic chemical compounds and blends of such compounds has been successful in this regard. Examples of such ingredients can be found in the International Cosmetic Ingredient Dictionary and Handbook, 10$^{th}$ Edition (2004).

Therefore, one of the problems associated with using malodorous skin-active ingredients is that additional chemical ingredients may have to be used to mask the unpleasant odors caused by the skin-active ingredient.

SUMMARY OF THE INVENTION

The inventors have discovered new uses of aromatic chemical compounds that have previously been thought to be useful only as odor neutralizing agents. In this regard, the inventors have identified certain aromatic chemical compounds that are cosmeceutically effective in treating skin or skin cells or preventing skin or skin cell damage while also being capable of reducing, masking, or preventing the intensity of malodorous smelling cosmetic compositions (e.g., aromatic skin-active ingredients or compounds). Therefore the compositions of the present invention can exclude or reduce the amount of odor neutralizing compounds in instances where an aromatic skin-active ingredient of the present invention is used. However, the inventors contemplate the use of odor neutralizing compounds in compositions that also include the aromatic skin-active ingredients disclosed throughout this specification.

In one non-limiting aspect, there is disclosed a method of treating or preventing a skin condition comprising topically applying a composition that includes an aromatic skin-active ingredient on skin, wherein the topical application of the composition treats or prevents the skin condition. In certain embodiments, a cosmeceutically effective amount of the aromatic skin-active ingredient is applied on the skin. Non-limiting examples of a cosmeceutically effective amount include 0.005% to 2.0% by weight of the composition (note that other ranges are contemplated and disclosed throughout this specification). In certain non-limiting aspects, the aromatic skin-active ingredient can be selected from the group consisting of those identified in Table 1 below (e.g., 1,4-dioxacycloheptadecane-5,17-dione; (3E)-4-(2,6,6-trimethylcyclohex-1-en-1-yl)but-3-en-2-one; 1-(1,2,3,4,5,6,7,8-octahydro-2,3,8,8-tetramethyl-2-naphthalenyl)ethan-1-one; 1-(2,3,8,8-tetramethyl-1,2,3,5,6,7,8,8a-octahydronaphthalen-2-yl)ethanone; 1-(2,3,8,8-tetramethyl-1,2,3,4,6,7,8,8a-octahydronaphthalen-2-yl)ethanone; 4-methyl-3-decen-5-ol; 2,6-dimethyl-5-heptenal; 3,3-dimethyl-5(2,2,3-trimethyl-3-cyclopenten-1-yl)-4-penten-2-ol; 3-hexen-1-ol (E) and (Z); methyl 3-oxo-2-pentylcyclopentanecarboxylate; 4-ethyl-3,7-dimethylocta-1,6-dien-3-ol; 2-isobutyl-4-methyltetrahydro-2H-pyran-4-ol; α-methyl-1,3-benzodioxole-5-propionaldehyde; 5-heptyldihydrofuran-2(3H)-one; 3-(4-isopropylphenyl)-2-methylpropanal; 2-methyldecanal; 2,4-nonadien-1-al; 2-dodecenal (E); 2,6-nonadien-1-al (trans, trans; trans, cis); 1-dodecanal; 4-tert-butylcyclohexyl acetate; methyl non-2-enoate; 1-methyl-3-(4-methylpent-3-enyl)cyclohex-3-enecarbaldehyde; 3a,4,5,6,7,7a-hexahydro-4,7-methano-1h-inden-5(or 6)-yl acetate; 3-(4-ethylphenyl)-2,2-dimethylpropanal; 3-(2-ethylphenyl)-2,2-dimethylpropanal; (Z)-4-methyl-3H-benzo[c][1,2]dioxepin-3-one; cis-2-hexenyl acetate; (Z)-2-(but-2-enyl)-3-methylcyclopent-2-enone; methyl 2,2-dimethyl-6-methylenecyclohexanecarboxylate; (Z)-5-(hydroxyimino)octan-3-one; (2,4,6-)trimethyl-3-cyclohexene-1-carboxaldehyde; (3,5,6-)trimethyl-3-cyclohexene-1-carboxaldehyde; 5-pentyldihydrofuran-2(3H)-one; cis-6-nonenal; ethyl 3-isopropylbicyclo[2.2.1]hept-5-ene-2-carboxylate; and 3,7-dimethyl-6-octen-1-yl acetate). The composition can include a single aromatic skin-active ingredient or any combination of aromatic skin active ingredients. By way of example, the composition can include at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 of the aromatic skin-active ingredients, including any combination thereof. Non-limiting examples of skin conditions include pruritus, spider veins, lentigo, age spots, senile purpura, keratosis, melasma, blotches, fine lines or wrinkles, nodules, sun damaged skin, dermatitis (including, but not limited to seborrheic dermatitis, nummular dermatitis, contact dermatitis, atopic dermatitis, exfoliative dermatitis, perioral dermatitis, and stasis dermatitis), psoriasis, folliculitis, rosacea, acne, impetigo, erysipelas, erythrasma, eczema, and other inflammatory skin conditions. In certain non-limiting aspects, the skin condition can be caused by exposure to UV light, age, irradiation, chronic sun exposure, environmental pollutants, air pollution, wind, cold, heat, chemicals, disease pathologies, smoking, or lack of nutrition. The skin can be facial skin or non-facial skin (e.g., arms, legs, hands, chest, back, feet, etc.). The method can further comprise identifying a person in need of skin treatment. The person can be a male or female. The age of the person can be at least 1, 2, 3, 4, 5, 6, 7, 8, 9, 10, 15, 20, 25, 30, 35, 40, 45, 50, 55, 60, 65, 70, 75, 80, 85, 90, 95, or more years old, or any range derivable therein. In another aspect, the method can include topically applying an amount effective to: increase the stratum corneum turnover rate of the skin; increase collagen synthesis in fibroblasts; increase cellular anti-oxidant defense mechanisms (e.g., exogenous additions of anti-oxidants can bolster, replenish, or prevent the loss of cellular antioxidants such as catalase and glutathione in skin cells (e.g., keratinocytes, melanocytes, langerhans cells, etc.); inhibit melanin production in melanocytes; reduce or prevent oxidative damage to skin (including reducing the amount lipid peroxides and/or protein oxidation in the skin).

In another aspect, there is disclosed a method of reducing or preventing lipoxygenase, cyclooxygenase (COX), tumor necrosis factor-alpha (TNF-α), or matrix metalloproteinase (MMP) enzyme activity in a cell comprising contacting the cell with an aromatic skin-active ingredient, wherein contacting the cell with the aromatic ingredient reduces or prevents lipoxygenase, cyclooxygenase (COX), tumor necrosis factor-alpha (TNF-α), or matrix metalloproteinase (MMP) enzyme activity in the cell. Also disclosed is a method of reducing or preventing oxidative damage in a cell comprising contacting the cell with an aromatic skin-active ingredient, wherein contacting the cell with the aromatic ingredient reduces oxidative damage in the cell. The cell can be a skin cell. Non-limiting examples of skin cells include human epidermal keratinocytes, human dermal fibroblasts, or human melanocytes. Non-limiting examples of cyclooxygenase include cyclooxygenase-1 or cyclooxygenase-2. Non-limiting examples of matrix metalloproteinase enzyme include MMP3 or MMP9. The aromatic skin-active ingredient can be selected from the group consisting of those identified in Table I below. The aromatic skin-active ingredient is comprised in a composition. The cells can be contacted with a single aromatic skin-active ingredient or any combination of aromatic skin active ingredients. By way of example, the cells can be contacted with at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 of the aromatic skin-active ingredients, including any combination thereof.

In a particular aspect there is disclosed a method of treating a fine line or wrinkle comprising topically applying to a fine line or wrinkle on skin a composition comprising 3-hexen-l-ol, 4-methyl-3-decen-5-ol, and (3E)-4-(2,6,6-trimethylcyclohex-1-en- 1 -yl)but-3-en-2-one, wherein MMP-9 activity is reduced in a skin cell of the skin and treats said fine line or wrinkle.

In certain embodiments, compositions of the present invention can decrease the amount of internal oxidation and/or external oxidative damage in a cell. In other aspects, the compositions can increase collagen synthesis in a cell. The compositions can also reduce skin inflammation, such as by reducing inflammatory cytokine production in a cell. Non-limiting examples of such cells include human epidermal keratinocyte, human fibroblast dermal cell, human melanocytes, three dimensional human cell-derived in vitro tissue equivalents comprising human keratinocytes, human fibroblasts, or human melanocytes, or any combination thereof (e.g., combination of human keratinocytes and human fibroblasts or a combination of human keratinocytes and human melanocytes).

Also disclosed is a method of lightening skin or evening skin tone comprising applying the compositions of the present invention to the skin. The method can further comprise identify a person in need of lightening skin or evening skin tone. The methods can further include inhibiting melanogenesis in a skin cell, inhibiting tyrosinase or tyrosinase synthesis in a skin cell, or inhibiting melanin transport to keratinocytes in a skin cell. The composition can act as an alpha melanin stimulatory hormone antagonist. The composition can even out pigmentation of the skin. In non-limiting aspect, lightening skin can include reducing the appearance of an age spot, a skin discoloration, or a freckle.

Also disclosed is a method of treating hyperpigmentation comprising applying the compositions of the present invention to the skin. The method can also comprise identifying a person in need of treating hyperpigmentation. Additional methods contemplated by the inventor include methods for reducing the appearance of an age spot, a skin discoloration, or a freckle, reducing or preventing the appearance of fine lines or wrinkles in skin, or increasing the firmness of skin.

Another aspect of the present invention includes a composition comprising an effective amount of an aromatic skin-active ingredient or combination of such ingredients. The composition can be a topical skin-care composition. The aromatic skin-active ingredient can be selected from the group consisting of those identified in Table 1 below. The composition can be fragrance free. In certain aspects, the composition does not include another aromatic compound. The composition does not include another skin-active ingredient in certain embodiments and/or does not include another aromatic compound. The composition can include a single aromatic skin-active ingredient or any combination of aromatic skin active ingredients. By way of example, the composition can include at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 of the aromatic skin-active ingredients, including any combination thereof. The combination of the aromatic skin-active ingredients can work together synergistically or in a complementary fashion to produce effects that exceed the effects of what would be expected if the extracts were used in separate compositions. Non-limiting synergistic effects include the reduction of internal or external oxidative damage, increased collagen production, reduction in inflammatory responses and the inhibition of melanogenesis, or reduce or prevent lipoxygenase, cyclooxygenase (COX), tumor necrosis factor-alpha (TNF-α), or matrix metalloproteinase (MMP) enzyme activity in a skin cell. In certain embodiments, the compositions are formulated into topical skin care compositions. The compositions can be cosmetic compositions. In other aspects, the compositions can be formulated as emulsions (e.g., oil-in-water and water-in-oil emulsions), creams, lotions, solutions (e.g., aqueous or hydro-alcoholic solutions), anhydrous bases (e.g., lipstick or a powder), gels, and ointments. In other non-limiting embodiments, the compositions of the present invention can be included in anti-aging, cleansing, or moisturizing products. The compositions can also be formulated for topical skin application at least 1, 2, 3, 4, 5, 6, 7, or more times a day during use. In other aspects of the present invention, compositions can be storage stable or color stable, or both. It is also contemplated that the viscosity of the composition can be selected to achieve a desired result (e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000 cps, etc. as measured on a Brookfield Viscometer using a TC spindle at 2.5 rpm at 25° C.). The compositions of the present invention can also be modified to have a desired oxygen radical absorbance capacity (ORAC) value. In certain non-limiting aspects, the compositions of the present invention can be modified to have an ORAC value per mg of at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 70, 80, 90, 95, 100, 200, 300, 400, 500, 600, 700, 800, 900, 1000, 2000, 3000, 4000, 5000, 6000, 7000, 8000, 9000, 10000, 15000, 20000, 30000, 50000, 100000 or more or any range derivable therein. The compositions in non-limiting aspects can have a pH of about 6 to about 9. In other aspects, the pH can be 1, 2, 3, 4, 5, 6, 7, 8, 9, 10, 11, 12, 13, or 14. In other aspects, the compositions can be sunscreens having a sun protection factor (SPF) of 1, 5, 10, 15, 20, 25, 30, 35, 40, 45, 50, 55, or more. In certain aspects, the compositions include odor neutralizing ingredients other than the aromatic skin-active ingredients disclosed throughout this specification.

Also contemplated are kits that includes the compositions of the present invention. In certain embodiments, the composition is comprised in a container. The container can be a bottle, dispenser, or package. The container can dispense a pre-determined amount of the composition. In certain aspects, the compositions is dispensed in a spray, dollop, or liquid. The container can include indicia on its surface. The indicia can be a word, an abbreviation, a picture, or a symbol.

Also contemplated is a product comprising a composition of the present invention. In non-limiting aspects, the product can be a cosmetic product. The cosmetic product can be those described in other sections of this specification or those known to a person of skill in the art. Non-limiting examples of products include a moisturizer, a cream, a lotion, a skin softener, a foundation, a night cream, a lipstick, a cleanser, a toner, a sunscreen, a mask, or an anti-aging product.

It is contemplated that any embodiment discussed in this specification can be implemented with respect to any method or composition of the invention, and vice versa. Furthermore, compositions of the invention can be used to achieve methods of the invention.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The terms "inhibiting" or "reducing" or any variation of these terms, when used in the claims and/or the specification includes any measurable decrease or complete inhibition to achieve a desired result.

The term "effective," as that term is used in the specification and/or claims, means adequate to accomplish a desired, expected, or intended result. For instance, an "effective amount" or a "cosmeceutically effective amount" or a "therapeutically effective amount" means an amount that is adequate to accomplish a desired, expected, or intended result. Use of an aromatic skin-active ingredient(s) in the methods and compositions of the present invention can include an "effective amount" or a "cosmeceutically effective amount" or a "therapeutically effective amount." Such amounts can vary depending on the aromatic skin-active ingredient(s), the condition to be treated or prevented and its severity, the manner of administration, and the age of the person to be treated, but can be determined routinely by one of ordinary skill in the art having regard to his own knowledge and to this disclosure.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

In today's image conscious society, people are continually looking for a product that can improve the visual appearance of their skin. Often times, aged skin, uneven skin tone, or skin damaged by environmental factors such as UV light, chronic sun exposure, environmental pollutants, chemicals, disease pathologies, or smoking, is associated with unattractive skin. Previous attempts to improve the visual appearance of skin often involved the use of skin-active ingredients that have an unpleasant or malodorous smell.

The inventors have discovered new uses of aromatic chemical compounds that have previously been thought to be useful only as odor neutralizing agents. As explained in non-limiting aspects in the following sections, the aromatic skin-active ingredients discovered by the inventors have been shown to be effective at treating a wide range of skin ailments and preventing skin damage. These compounds can be incorporated into all types of cosmetic compositions. These and other aspect of the present invention are described in further non-limiting detail below.

A. Aromatic Skin-Active Ingredients

The inventor has discovered that the compounds listed in Table 1 have surprising and unexpected properties that are beneficial to human skin. Data supporting these properties (including how these data were obtained) are presented in the EXAMPLES section below which is incorporated into this section by reference. The beneficial properties of these compounds range from reducing or preventing oxidative damage to skin or skin cells, reducing or preventing lipoxygenase activity in skin or skin cells, reducing or inhibiting cyclooxygenase (COX) activity in skin or skin cells, reducing or inhibiting tumor necrosis factor alpha (TNF-$\alpha$) in skin or skin cells, and reducing or inhibiting matrix metalloproteinase (MMP) enzyme activity in skin or skin cells.

TABLE 1

(Aromatic Skin-Active Ingredients)

| Structure | CAS # | Chemical Name (alternate name) |
|---|---|---|
| $C_{15}H_{26}O_4$ 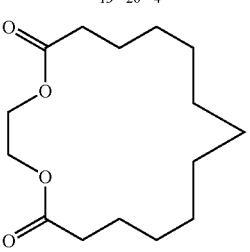 | 105-95-3 | 1,4-dioxacycloheptadecane-5,17-dione (Ethylene Brassylate) |
| $C_{13}H_{20}O$ 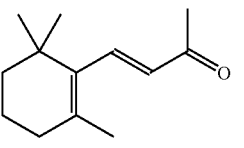 | 14901-07-6 | (3E)-4-(2,6,6-trimethylcyclohex-1-en-1-yl)but-3-en-2-one (Beta Ionone) |
| $C_{16}H_{26}O$ 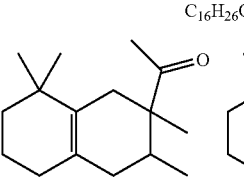 (mixture) | 54464-57-2, 68155-66-8 and 68155-67-9 | 1-(1,2,3,4,5,6,7,8-octahydro-2,3,8,8-tetramethyl-2-naphthalenyl)ethan-1-one; 1-(2,3,8,8-tetramethyl-1,2,3,5,6,7,8,8a-octahydronaphthalen-2-yl)ethanone; and 1-(2,3,8,8-tetramethyl-1,2,3,4,6,7,8,8a-octahydronaphthalen-2-yl)ethanone (Iso E super) |
| $C_{11}H_{22}O$ 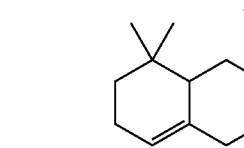 | 81782-77-6 | 4-methyl-3-decen-5-ol |
| $C_9H_{16}O$ 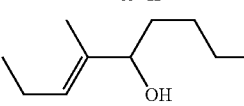 | 106-72-9 | 2,6-dimethyl-5-heptenal (Melanol) |
| $C_{15}H_{26}O$ 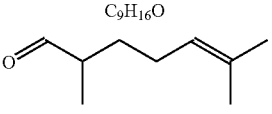 | 107898-54-4 | 3,3-dimethyl-5(2,2,3-trimethyl-3-cyclopenten-1-yl)-4-penten-2-ol (Polysantol) |
| $C_6H_{12}O$ 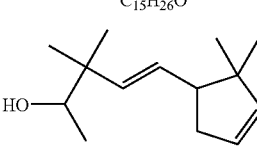 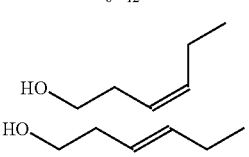 | 928-96-1 | 3-hexen-1-ol (E) and (Z) |

TABLE 1-continued (Aromatic Skin-Active Ingredients)

| Structure | CAS # | Chemical Name (alternate name) |
|---|---|---|
| $C_{13}H_{22}O_3$ 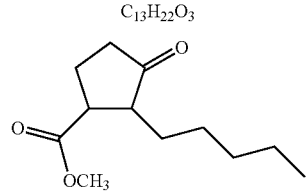 | 24851-98-7 | methyl 3-oxo-2-pentylcyclopentane-carboxylate (Methyl Dihydro Jasmonate) |
| $C_{12}H_{22}O$ 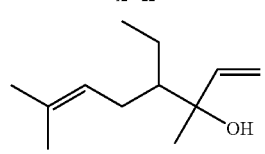 | 10339-55-6 | 4-ethyl-3,7-dimethylocta-1,6-dien-3-ol (Ethyl Linalool) |
| $C_{10}H_{20}O_2$ 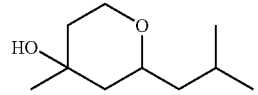 | 63500-71-0 | 2-isobutyl-4-methyltetrahydro-2H-pyran-4-ol (Florol) |
| $C_{11}H_{12}O_3$ 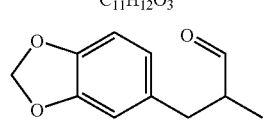 | 1205-17-0 | α-methyl-1,3-benzodioxole-5-propionaldehyde (Helional) |
| $C_{11}H_{20}O_2$ 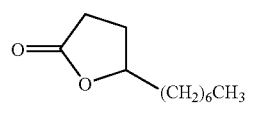 | 104-67-6 | 5-heptyldihydrofuran-2(3H)-one (Aldehyde C-14) |
| $C_{13}H_{18}O$ 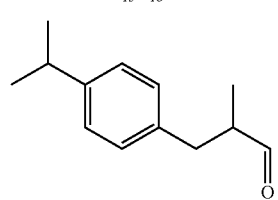 | 103-95-7 | 3-(4-isopropylphenyl)-2-methylpropanal (Cyclamen Aldehyde) |
| $C_{11}H_{22}O$ 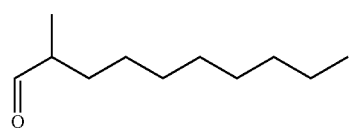 | 19009-56-4 | 2-methyldecanal (Aldehyde C-11 MOA) |
| $C_9H_{14}O$ 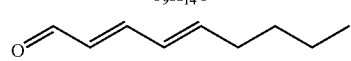 | 5910-87-2 | 2,4-nonadien-1-al |
| $C_{12}H_{22}O$ 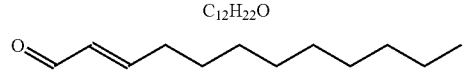 | 20407-84-5 | 2-dodecenal (E) (trans-2-dodecenal) |
| $C_{12}H_{24}O$ 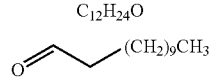 | 112-54-9 | 1-dodecanal (Aldehyde C-12 Lauric) |

TABLE 1-continued (Aromatic Skin-Active Ingredients)

| Structure | CAS # | Chemical Name (alternate name) |
|---|---|---|
| $C_9H_{14}O$ 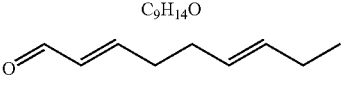 (separately or mixture) | 557-48-2 and 17587-33-6 | 2,6-nonadien-1-al (trans, trans; trans, cis) |
| $C_{12}H_{22}O_2$ 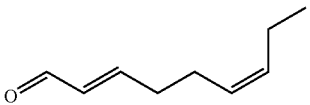 | 32210-23-4 | 4-tert-butylcyclohexyl acetate (Vertenex ® H.C.) |
| $C_{10}H_{18}O_2$ 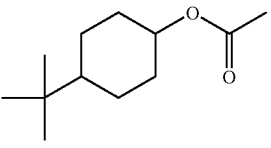 | 111-79-5 | methyl non-2-enoate (Neofolione) |
| $C_{14}H_{22}O$ 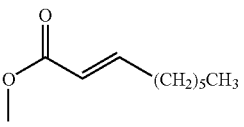 | 52474-60-9 | 1-methyl-3-(4-methylpent-3-enyl)cyclohex-3-enecarbaldehyde (Precyclemone B) |
| $C_{12}H_{16}O_2$ 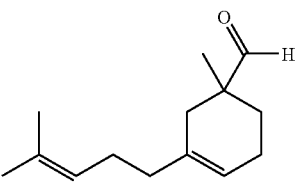 or 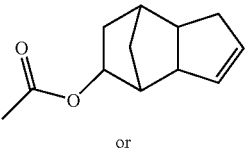 | 54830-99-8 | 3a,4,5,6,7,7a-hexahydro-4,7-methano-1h-inden-5(or 6)-yl acetate (Cyclacet) |
| $C_{13}H_{18}O$ 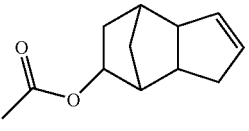 | 67634-15-5 and 67634-14-4 | 3-(4-ethylphenyl)-2,2-dimethylpropanal and 3-(2-ethylphenyl)-2,2-dimethylpropanal (Floralozone) |

TABLE 1-continued (Aromatic Skin-Active Ingredients)

| Structure | CAS # | Chemical Name (alternate name) |
|---|---|---|
| 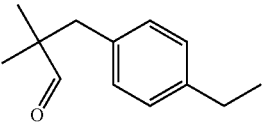 (mixture) | | |
| $C_{10}H_8O_3$ 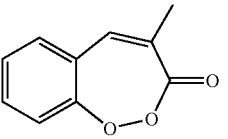 | 28940-11-6 | (Z)-4-methyl-3H-benzo[c][1,2]dioxepin-3-one (Calone 1951) |
| $C_8H_{14}O_2$ 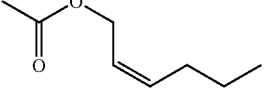 | 3681-71-8 | cis-2-hexenyl acetate (Leaf Acetate) |
| $C_{10}H_{14}O$ 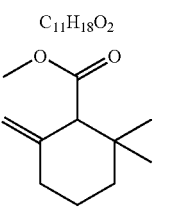 | 1128-08-1 | (Z)-2-(but-2-enyl)-3-methylcyclopent-2-enone (Dihydro-jasmone) |
| $C_{11}H_{18}O_2$ 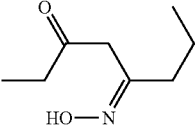 | 81752-87-6 | methyl 2,2-dimethyl-6-methylenecyclohexane-carboxylate (Romascone ®) |
| $C_8H_{15}NO_2$ 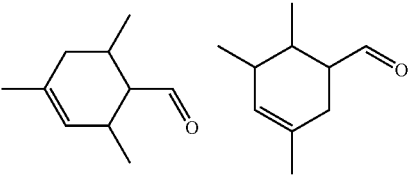 | 22457-23-4 | (Z)-5-(hydroxyimino)octan-3-one (Stemone) |
| $C_{10}H_{16}O$ 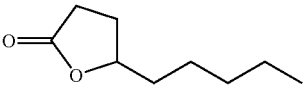 (mixture) | 1335-66-6 and 67634-07-5 | (2,4,6-)trimethyl-3-cyclohexene-1-carboxaldehyde and (3,5,6-)trimethyl-3-cyclohexene-1-carboxaldehyde (Iso Cyclo Citral) |
| $C_9H_{16}O_2$ | 104-61-0 | 5-pentyldihydrofuran-2(3H)-one (Aldehyde C-18) |

TABLE 1-continued (Aromatic Skin-Active Ingredients)

| Structure | CAS # | Chemical Name (alternate name) |
|---|---|---|
| $C_9H_{16}O$ | 2277-19-2 | cis-6-nonenal |
| $C_{13}H_{20}O_2$ | 116126-82-0 | ethyl 3-isopropylbicyclo[2.2.1]hept-5-ene-2-carboxylate (Herbanante) |
| $C_{12}H_{22}O_2$ | 150-84-5 | 3,7-dimethyl-6-octen-1-yl acetate (citronellyl acetate) |

The aromatic skin-active compounds and derivatives and modifications of the same can be prepared by using convention chemical synthesis techniques (see, e.g., Organic Chemistry, $5^{th}$ Ed., which is incorporated by reference).

1. Oxidative Damage in Skin Cells

Free radicals are chemically active molecular fragments that have a charge due to excess or a deficient number of electrons. Reactive oxygen species (ROS), free radicals containing oxygen, generate oxidative damage to human skin cells through endogenous (cellular) and exogenous (environmental) mechanisms. In aged skin, oxidative damage accumulates which results in lost skin elasticity and increased fine lines and wrinkles. Antioxidants block the oxidation process by neutralizing, or reduce, this energy to protect cellular functions and prevent damage to cell proteins. Thus, reductions in oxidative damage in skin can reduce the signs of signs of premature aging.

2. Lipoxygenase

Lipoxygenase enzymes catalyze the oxidative conversion of arachadonic acid to hydroxyeicosotrienenoic (HETE), that are subsequently converted to leukotrienes. Increased levels of arachadonic acid is associated with sustained inflammation in human skin. Thus, compounds which reduce the activity of lipoxygenase enzymes can act as a potent mediator of skin inflammation.

3. Cyclooxygenase (COX)

COX is a bifunctional enzyme exhibiting both cyclooxygenase and peroxidase activities. The cyclooxygenase activity converts arachadonic acid to a hydroperoxy endoperoxide (Prostaglandin G2; PGG2) and the peroxidase component reduces the endoperoxide (Prostaglandin H2; PGH2) to the precursor of prostaglandins, thromboxanes, and prostacyclins, key mediators of skin inflammation. Thus, compounds which reduce the enzymatic activity of COX will also mediate the inflammatory response in skin.

4. Tumor Necrosis Factor-Alpha (TNF-α)

TNF-α is a pleiotropic cytokine that plays a central role in inflammation. Increase in its expression is associated with an up regulation in pro-inflammatory activity. Thus, compounds that reduce the secretion of TNF-α protein by human epidemial keratinocytes reduce the inflammatory response resulting in reduced skin redness and irritation.

5. Matrix Metalloproteinases (MMPs)

MMPs are extracellular proteases whose substrates include the extracellular matrix proteins which comprise the skin dermal compartment. MMP3 substrates include collagens, fibronectins, and laminin, while MMP9 substrates include collagen VII, fibronectin, and laminin. In aging skin, the these enzymes work to destroy the proteins which provide support for the skin. Therefore, reduction in the activity of these enzymes inhibits the destruction of these proteins. Thus, compounds which inhibit the activity of MMPs will result increased amounts of collagen and other dermal matrix proteins.

B. Derivatives and Modification of the Aromatic Skin-Active Ingredients

Derivatives and modifications to the aromatic skin-active ingredients of the present invention are also contemplated in the context of the present invention. Non-limiting examples of modifications that can be made to such ingredients include the addition or removal of lower alkyls such as methyl, ethyl, propyl, or substituted lower alkyls such as hydroxymethyl or aminomethyl groups; carboxyl groups and carbonyl groups; hydroxyls; nitro, amino, amide, and azo groups; sulfate, sulfonate, sulfono, sulfhydryl, sulfonyl, sulfoxido, phosphate, phosphono, phosphoryl groups, and halide substituents. Additional modifications can include an addition or a deletion of one or more atoms of the atomic framework, for example, substitution of an ethyl by a propyl; and substitution of a phenyl by a larger or smaller aromatic group. Alternatively, in a cyclic or bicyclic structure, hetero atoms such as N, S, or O can be substituted into the structure instead of a carbon atom.

C. Compositions of the Present Invention

1. Combinations and Amounts of Ingredients

It is contemplated that the compositions of the present invention can include any number of combinations of the aromatic skin-active ingredients disclosed throughout this specification. Additionally, the compositions can include any number of combinations of additional ingredients described throughout this specification. The concentrations of the aromatic skin-active ingredients and additional ingredients can vary. In non-limiting embodiments, for example, the compositions can include in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or more, or any range or integer derivable therein, of at least one of the aromatic skin-active ingredients or additional ingredients. In non-limiting aspects, the percentage of such ingredients can be calculated by weight or volume of the total weight of the compositions. The concentrations can vary depending on the desired effect of the compositions or on the product into which the compositions are incorporated.

2. Composition Vehicles

The compositions of the present invention can be formulated into all types of vehicles. Non-limiting examples of suitable vehicles include emulsions (e.g., water-in-oil, water-in-oil-in-water, oil-in-water, oil-in-water-in-oil, oil-in-water-in-silicone emulsions), creams, lotions, solutions (both aqueous and hydro-alcoholic), anhydrous bases (such as lipsticks and powders), gels, and ointments or by other method or any combination of the forgoing as would be known to one of ordinary skill in the art (Remington's, 1990). Variations and other appropriate vehicles will be apparent to the skilled artisan and are appropriate for use in the present invention. In certain aspects, the concentrations and combinations of the ingredients be selected in such a way that the combinations are chemically compatible and do not form complexes which precipitate from the finished product.

It is also contemplated that aromatic skin-active ingredients and additional ingredients identified throughout this specification can be encapsulated for delivery to a target area such as skin. Non-limiting examples of encapsulation techniques include the use of liposomes, vesicles, and/or nanoparticles (e.g., biodegradable and non-biodegradable colloidal particles comprising polymeric materials in which the ingredient is trapped, encapsulated, and/or absorbed—examples include nanospheres and nanocapsules) that can be used as delivery vehicles to deliver such ingredients to skin (see, e.g., U.S. Pat. No. 6,387,398; U.S. Pat. No. 6,203,802; U.S. Pat. No. 5,411,744; Kreuter 1998).

Also contemplated are pharmaceutically-acceptable or pharmacologically-acceptable compositions. The phrase "pharmaceutically-acceptable" or "pharmacologically-acceptable" includes compositions that do not produce an allergic or similar untoward reaction when administered to a human. Typically, such compositions are prepared either as topical compositions, liquid solutions or suspensions, solid forms suitable for solution in, or suspension in, liquid prior to use can also be prepared. Routes of administration can vary with the location and nature of the condition to be treated, and include, e.g., topical, inhalation, intradermal, transdermal, parenteral, intravenous, intramuscular, intranasal, subcutaneous, percutaneous, intratracheal, intraperitoneal, intratumoral, perfusion, lavage, direct injection, and oral administration and formulation.

3. Products

The compositions of the present invention can be incorporated into products. Non-limiting examples of products include cosmetic products, food-based products, pharmaceutical products, etc. By way of example only, non-limiting cosmetic products include sunscreen products, sunless skin tanning products, hair products, fingernail products, moisturizing creams, skin benefit creams and lotions, softeners, day lotions, gels, ointments, foundations, night creams, lipsticks, mascaras, eyeshadows, eyeliners, cheek colors, cleansers, toners, masks, or other known cosmetic products or applications. Additionally, the cosmetic products can be formulated as leave-on or rinse-off products.

4. Additional Ingredients

Compositions of the present invention can include additional ingredients. Non-limiting examples of additional ingredients include cosmetic ingredients (both active and non-active) and pharmaceutical ingredients (both active and non-active).

a. Cosmetic Ingredients

The CTFA International Cosmetic Ingredient Dictionary and Handbook (2004) describes a wide variety of non-limiting cosmetic ingredients that can be used in the context of the present invention. Examples of these ingredient classes include: fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, emulsifiers, stabilizers, lubricants, solvents, moisturizers (including, e.g., emollients, humectants, film formers, occlusive agents, and agents that affect the natural moisturization mechanisms of the skin), water-repellants, UV absorbers (physical and chemical absorbers such as paraminobenzoic acid ("PABA") and corresponding PABA derivatives, titanium dioxide, zinc oxide, etc.), essential oils, vitamins (e.g., A, B, C, D, E, and K), trace metals (e.g., zinc, calcium and selenium), anti-irritants (e.g., steroids and non-steroidal antiinflammatories), botanical extracts (e.g., aloe vera, chamomile, cucumber extract, ginkgo biloba, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., glycerin, propylene glycol, butylene glycol, pentylene glycol, sorbitol, urea, and manitol), exfoliants (e.g., alpha-hydroxyacids, and beta-hydroxyacids such as lactic acid, glycolic acid, and salicylic acid; and salts thereof) waterproofing agents (e.g., magnesium/aluminum hydroxide stearate), skin conditioning agents (e.g., aloe extracts, allantoin, bisabolol, ceramides, dimethicone, hyaluronic acid, and dipotassium glycyrrhizate), thickening agents (e.g., substances which that can increase the viscosity of a composition such as carboxylic acid polymers, crosslinked polyacrylate polymers, polyacrylamide polymers, polysaccharides, and gums), and silicone containing compounds (e.g., silicone oils and polyorganosiloxanes).

b. Pharmaceutical Ingredients

Pharmaceutical ingredients are also contemplated as being useful with the emulsion compositions of the present invention. Non-limiting examples of pharmaceutical ingredients include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

D. Kits

Kits are also contemplated as being used in certain aspects of the present invention. For instance, a composition of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of a composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for using the kit and/or compositions. Instructions can include an explanation of how to apply, use, and maintain the compositions.

EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Efficacy Data for the Aromatic-Skin Active Ingredients

The following Tables 2-4 provide data confirming the efficacy of the aromatic skin-active ingredients identified in Table 1 above:

TABLE 2

| Aromatic Skin-Active Ingredient (alternate name) | Cox-1 Inhibition (0.020%) | Cox-2 Inhibition (0.001%) | LO Inhibition (0.1%) | MMP3 Inhibition (0.001%) | MMP9 Inhibition (0.001%) | TNF-α Inhibition (0.01%) |
|---|---|---|---|---|---|---|
| Aldehyde C-11 MOA | | | | | | −38.68% |
| 2,4-nonadien-1-al | | −21.15% | | −23.75% | −19.87% | |
| 2-dodecenal (E) | | | | | −24.98% | |
| Aldehyde C-12 Lauric | | | | | −27.64% | |
| Beta Ionone | | | | | −19.82% | |
| 2,6-nonadien-1-al | −11.42% | −17.58% | −45.58% | −20.34% | −32.53% | |
| Vertenex ® H.C. | −18.50% | | −37.86% | | | |
| Neofolione | | | −27.46% | | | −53.90% |
| Precyclemone B | | | | −25.09% | | |
| Cyclacet | | | −26.37% | | | |
| Melanol | | | −20.45% | | | |
| Floralozone | | | | | | −33.20% |
| Calone 1951 | | | | −21.26% | | |

TABLE 3

| Aromatic Skin-Active Ingredient (alternate name) | Cox-2 Inhibition (0.001%) | MMP9 Inhibition (0.01%) |
|---|---|---|
| Leaf Acetate | | −22.04% |
| Dihydro-jasmone | −32.33% | −37.47% |
| Romascone ® | −23.31% | |
| Iso E super | −20.80% | |
| Stemone | −22.31% | |
| Polysantol | −36.09% | |
| 4-methyl-3-decen-5-ol | | −28.09% |
| Iso Cyclo Citral | −31.58% | −21.78% |
| 3-hexen-1-ol (E) and (Z) | −23.56% | −23.82% |
| Aldehyde C-18 | −22.56% | −22.22% |
| Ethylene Brassylate | −20.55% | −32.98% |
| Cis-6-Nonenal | −27.07% | −19.20% |
| Herbanante | −25.06% | −26.84% |
| Methyl Dihydro Jasmonate | | −33.78% |

TABLE 4

| Aromatic Skin-Active Ingredient (alternate name) | Cox-1 Inhibition (0.001%) | Cox-2 Inhibition (0.001%) | LO Inhibition (0.001%) | Antioxidant Properties (0.001%) |
|---|---|---|---|---|
| Citronellyl Acetate | −27.99% | −20.93% | | |
| Ethyl Linalool | | | | +23.62% |
| Aldehyde C-14 | | | −20.24% | |

Example 2

Assays to Assess Efficacy

The following assays were used to obtain the results identified in Tables 2-4.

Antioxidant (AO) assay: An in vitro bioassay that measures the total anti-oxidant capacity of compounds. The assay relies on the ability of antioxidants in the sample to inhibit the oxidation of ABTS® (2,2'-azino-di-[3-ethylbenzthiazoline sulphonate]) to ABTS®-+ by metmyoglobin. The antioxidant system of living organisms includes enzymes such as superoxide dismutase, catalase, and glutathione peroxidase; macromolecules such as albumin, ceruloplasmin, and ferritin; and an array of small molecules, including ascorbic acid, $\alpha$-tocopherol, $\beta$-carotene, reduced glutathione, uric acid, and bilirubin. The sum of endogenous and food-derived antioxidants represents the total antioxidant activity of the extracellular fluid. Cooperation of all the different antioxidants provides greater protection against attack by reactive oxygen or nitrogen radicals, than any single compound alone. Thus, the overall antioxidant capacity may give more relevant biological information compared to that obtained by the measurement of individual components, as it considers the cumulative effect of all antioxidants present in plasma and body fluids. This assay relies on the ability of antioxidants in the sample to inhibit the oxidation of ABTS® (2,2'-azino-di-[3-ethylbenzthiazoline sulphonate]) to ABTS®-+ by metmyoglobin. The capacity of the antioxidants in the sample to prevent ABTS oxidation is compared with that of Trolox, a water-soluble tocopherol analogue, and is quantified as molar Trolox equivalents.

Using an Anti-oxidant Assay kit (#709001; Cayman Chemicals), compounds were tested for their ability to inhibit oxidation of substrates in vitro. Positive values reflect the ability of compounds to inhibit oxidation and demonstrate anti-oxidant capabilities.

Lipoxygenase (LO) assay: An in vitro lipoxygenase (LO) inhibition assay. LOs are non-heme iron-containing dioxygenases that catalyze the addition of molecular oxygen to fatty acids. Linoleate and arachidonate are the main substrates for LOs in plants and animals. Arachadonic acid may then be converted to hydroxyeicosotrienenoic (HETE) acid derivatives, that are subsequently converted to leukotirenes, potent inflammatory mediators. This assay provides an accurate and convenient method for screening lipoxygenase inhibitors by measuring the hydroperoxides generated from the incubation of a lipoxygenase (5-, 12-, or 15-LO) with arachidonic acid.

Following manufacturer instructions for the Colorimetric LO Inhibitor screening kit (#760700, Cayman Chemical), purified 15-lipoxygenase and test compounds were mixed in assay buffer and incubated with shaking for 10 min at room temperature. Following incubation, arachidonic acid was added to initiate the reaction and mixtures incubated for an additional 10 min at room temperature. Colorimetric substrate was added to terminate catalysis and color progression was evaluated by fluorescence plate reading at 490 nm. The percent inhibition of lipoxyganse activity was calculated compared to non-treated controls to determine the ability of test compounds to inhibit the activity of purified enzyme.

Cyclooxygenase (COX) assay: An in vitro cyclooxygenase-1 and -2 (COX-1, -2) inhibition assay. COX is a bifunctional enzyme exhibiting both cyclooxygenase and peroxidase activities. The cyclooxygenase activity converts arachidonic acid to a hydroperoxy endoperoxide (Prostaglandin G2; PGG2) and the peroxidase component reduces the endoperoxide (Prostaglandin H2; PGH2) to the corresponding alcohol, the precursor of prostaglandins, thromboxanes, and prostacyclins. This COX Inhibitor Screening Assay measures the peroxidase component of cyclooxygenases. The peroxidase activity is assayed colorimetrically by monitoring the appearance of oxidized N,N,N',N'-tetramethyl-p-phenylenediamine (TMPD). This inhibitor screening assay includes both COX-1 and COX-2 enzymes in order to screen isozyme-specific inhibitors.

Following manufacturer instructions for the Colormetric COX (ovine) Inhibitor screening assay (#760111, Cayman Chemical), purified cyclooxygnase enzyme (COX-1 or COX-2), heme and test compounds were mixed in assay buffer and incubated with shaking for 15 min at room temperature. Following incubation, arachidonic acid and colorimetric substrate were added to initiate the reaction and incubated for an additional 15 min at room temperature with shaking. Color progression was evaluated by fluoresecence plate reading at 590 nm. The percent inhibition of COX-1 or COX-2 activity was calculated compared to non-treated controls to determine the ability of test compounds to inhibit the activity of purified enzyme.

Tumor necrosis factor alpha (TNF-$\alpha$) assay: The prototype ligand of the TNF superfamily, TNF-$\alpha$, is a pleiotropic cytokine that plays a central role in inflammation. Increase in its expression is associated with an up regulation in pro-inflammatory activity. This bioassay analyzes the effect of compounds on the production of TNF-$\alpha$ by human epidermal keratinocytes. The endpoint of this assay is a spectrophotometric measurement that reflects the presence of TNF-$\alpha$ and cellular viability. The assay employs the quantitative sandwich enzyme immunoassay technique whereby a monoclonal antibody specific for TNF-$\alpha$ has been pre-coated onto a microplate. Standards and samples are pipetted into the wells and any TNF-$\alpha$ present is bound by the immobilized antibody. After washing away any unbound substances, an enzyme-linked polyclonal antibody specific for TNF-$\alpha$ is added to the wells. Following a wash to remove any unbound antibody-enzyme reagent, a substrate solution is added to the wells and color develops in proportion to the amount of TNF-α bound in the initial step using a microplate reader for detection at 450 nm. The color development is stopped and the intensity of the color is measured.

Subconfluent normal human adult keratinocytes (Cascade Biologics) cultivated in EpiLife standard growth medium (Cascade Biologics) at 37° C. in 5% $CO_2$, were treated with PMA (10 ng/ml, Sigma Chemical, #P1585-1MG) and test compounds for 6 hours. PMA has been shown to cause a dramatic increase in TNF-α secretion which peaks at 6 hours after treatment. Following incubation, cell culture medium was collected and the amount of TNF-a secretion quantified using a sanwhich enzyme linked immuno-sorbant assay (ELISA) from R&D Systems (#DTA0° C.). Following all manufacturer instructions, medium from treated cells was incubated with antibodies directed against human TNF-α which were bound to microtiter plates. The amount of TNF-α protein was quantified by comparison of optical density units to standard concentrations of purified TNF-α protein. Values are calculated as % change in the amount of TNF-α protein secreted between control and treated samples. Negative values reflect the ability of test compounds to reduce the secretion of TNF-α under conditions known to induce skin irritation (PMA addition) compared to untreated controls.

Matrix metalloproteinase enzyme activity (MMP3; MMP9) assay: An in vitro matrix metalloprotease (MMP) inhibition assay. MMPs are extracellular proteases that play a role in many normal and disease states by virtue of their broad substrate specificity. MMP3 substrates include collagens, fibronectins, and laminin; while MMP9 substrates include collagen VII, fibronectins and laminin. Using Colorimetric Drug Discovery kits from BioMol International for MMP3 (AK-400) and MMP-9 (AK-410), this assay is designed to measure protease activity of MMPs using a thiopeptide as a chromogenic substrate (Ac-PLG-[2-mercapto-4-methyl-pentanoyl]-LG-$OC_2H5$)5,6. The MMP cleavage site peptide bond is replaced by a thioester bond in the thiopeptide. Hydrolysis of this bond by an MMP produces a sulfhydryl group, which reacts with DTNB [5,5'-dithiobis(2-nitrobenzoic acid), Ellman's reagent] to form 2-nitro-5-thiobenzoic acid, which can be detected by its absorbance at 412 nm ($\epsilon$=13,600 M-1 cm-1 at pH 6.0 and above 7). Data is reflected as % inhibition of the purified enzyme activity. Negative values demonstrate the ability of test compounds to inhibit the activity of MMPs compared to diluent controls.

Example 3

Compositions

Non-limiting examples of compositions of the present invention that can include an aromatic skin-active ingredient are described in Tables 5 and 6.

TABLE 5*

| Ingredient | % Concentration (by weight) |
|---|---|
| Phase A | |
| Water | 84.44 |
| Xanthum gum | 0.1 |
| M-paraben | 0.15 |
| P-paraben | 0.1 |
| Citric acid | 0.01 |

TABLE 5*-continued

| Ingredient | % Concentration (by weight) |
|---|---|
| Phase B | |
| Cetyl alcohol | 4.0 |
| Glyceryl stearate + PEG 100 | 4.0 |
| Octyl palmitate | 4.0 |
| Dimethicone | 1.0 |
| Tocopheryl acetate | 0.2 |
| Phase C** | |
| Aromatic Skin-Active Ingredient(s) | 2.0 |

*Procedure for making composition: Sprinkle Xanthum gum in water and mix for 10 min. Subsequently, add all ingredients in phase A and heat to 70-75° C. Add all items in phase B to separate beaker and heat to 70-75° C. Mix phases A and B at 70-75° C. Continue mixing and allow composition to cool to 30° C. Subsequently, add phase C ingredient while mixing.
**The aromatic skin-active ingredients identified throughout this specification can be incorporated into this composition. Additionally, any combination of such ingredients (including 2, 3, 4, 5, 6, 7, 8, 9, 10, 11, 12, 13, 14, 15, 16, 17, 18, 19, 20, 21, 22, 23, 24, 25, 26, 27, 28, 29, 30, or more) can be incorporated into a single composition. In such a case, the concentration ranges can be modified as desired or needed.

TABLE 6*

| Ingredient | % Concentration (by weight) |
|---|---|
| Phase A | |
| Water | 78.6 |
| M-paraben | 0.2 |
| P-paraben | 0.1 |
| Na2 EDTA | 0.1 |
| Shea butter | 4.5 |
| Petrolatum | 4.5 |
| Glycerin | 4.0 |
| Propylene Glycol | 2.0 |
| Finsolve TN | 2.0 |
| Phase B | |
| Sepigel 305 | 2.0 |
| Phase C** | |
| Aromatic Skin-Active Ingredient(s) | 2.0 |

*Add ingredients in phase A to beaker and heat to 70-75° C. while mixing. Subsequently, add the phase B ingredient with phase A and cool to 30° C. with mixing. Subsequently, add phase C ingredient while mixing.
**The aromatic skin-active ingredients identified throughout this specification can be incorporated into this composition. Additionally, any combination of such ingredients (including 2, 3, 4, 5, 6, 7, 8, 9, 10, 11, 12, 13, 14, 15, 16, 17, 18, 19, 20, 21, 22, 23, 24, 25, 26, 27, 28, 29, 30, or more) can be incorporated into a single composition. In such a case, the concentration ranges can be modified as desired or needed.

Example 4

Determining Efficacy of the Compositions of the Present Invention

The efficacy of compositions of the present inventions can be determined by methods known to those of ordinary skill in the art. The following are non-limiting procedures that can be used in the context of the present invention. It should be recognized that other testing procedures can be used, including, for example, objective and subjective procedures.

Skin moisture/hydration can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72° C.). Three separate impedance readings can be taken on each side of the face, recorded, and averaged. The T5 setting can be used on the impedance meter which averages the impedance values of every five seconds application to the face. Changes can be reported with statistical variance and significance.

Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether a composition is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b^2)^{1/2}$.

Skin dryness, surface fine lines, skin smoothness, and skin tone can be evaluated with clinical grading techniques. For example, clinical grading of skin dryness can be determined by a five point standard Kligman Scale: (O) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical grading of skin tone can be performed via a ten point analog numerical scale: (10) even skin of uniform, pinkish brown color. No dark, erythremic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations were made independently by two clinicians and averaged.

Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and the are of the replicas covered by wrinkles or fine lines was determined.

The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: $R_a$=Standardize roughness; $l_m$=the traverse (scan) length; and y=the absolute value of the location of the profile relative to the mean profile height (x-axis).

In other non-limiting aspects, the efficacy of the compositions of the present invention can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing the compositions and whitening agents of the present invention or with the base alone as a control. Alternatively, an untreated sample of the skin analog can be used as a control.

Oxygen Radical Absorption (or Absorbance) Capacity (ORAC) of the aromatic skin-active ingredients and compositions can also be assayed by measuring the antioxidant activity of such ingredients or compositions. This assay can quantify the degree and length of time it takes to inhibit the action of an oxidizing agent such as oxygen radicals that are known to cause damage cells (e.g., skin cells). The ORAC value of the aromatic skin-active ingredients and compositions can be determined by methods known to those of ordinary skill in the art (see U.S. Publication Nos. 2004/0109905 and 2005/0163880; Cao et al. (1993)), all of which are incorporated by reference). In summary, the assay described in Cao et al. (1993) measures the ability of antioxidant compounds in test materials to inhibit the decline of B-phycoerythrm (B-PE) fluorescence that is induced by a peroxyl radical generator, AAPH.

All of the aromatic skin-active ingredients, compositions, or methods disclosed and claimed in this specification can be made and executed without undue experimentation in light of the present disclosure. While the aromatic skin-active ingredients, compositions, or methods of this invention have been described in terms of particular embodiments, it will be apparent to those of skill in the art that variations may be applied to the aromatic skin-active ingredients, compositions, or methods and in the steps or in the sequence of steps of the method described herein without departing from the concept, spirit and scope of the invention.

REFERENCES

The following references, to the extent that they provide exemplary procedural or other details supplementary to those set forth herein, are specifically incorporated herein by reference.

U.S. Pat. No. 5,411,744
U.S. Pat. No. 6,203,802
U.S. Pat. No. 6,387,398
U.S. Patent Publn. 2004/0109905
U.S. Patent Publn. 2005/0163880
Cao et al., *Free Radic. Biol. Med.,* 14:303-311, 1993.
International Cosmetic Ingredient Dictionary, 10th edition, 2004.
Kreuter, *J. Microencapsulation,* 5:115-127, 1988.
*Organic Chemistry,* 5$^{th}$ Ed.
Packman and Gams, *J. Soc. Cos. Chem.,* 29:70-90, 1978.
Remington's Pharmaceutical Sciences, 18th Ed. Mack Printing Company, 1289-1329, 1990.

The invention claimed is:

1. A method of treating a fine line or wrinkle comprising topically applying to a fine line or wrinkle on skin a composition comprising 3-hexen-l-ol, 4-methyl-3-decen-5-ol, and (3E)-4-(2,6,6-trimethylcyclohex-l-en-l-yl)but-3-en-2-one, each applied in an amount effective to reduce MMP-9 activity in a skin cell of the skin, wherein the composition treats said fine line or wrinkle.

2. The method of claim 1, wherein the composition is an emulsion, a cream, or a lotion.

* * * * *